United States Patent [19]

Kirchner

[11] Patent Number: 5,214,819
[45] Date of Patent: Jun. 1, 1993

[54] TOOTHBRUSH WITH A BRUSH HEAD MOVED BY AN ELECTROMOTIVE DRIVE MEANS

[75] Inventor: Horst Kirchner, Eschborn, Fed. Rep. of Germany

[73] Assignee: Braun Aktiengesellschaft, Frankfurt, Fed. Rep. of Germany

[21] Appl. No.: 761,958

[22] PCT Filed: Mar. 3, 1990

[86] PCT No.: PCT/DE90/00153

§ 371 Date: Oct. 4, 1991

§ 102(e) Date: Oct. 4, 1991

[87] PCT Pub. No.: WO90/11703

PCT Pub. Date: Oct. 18, 1990

[30] Foreign Application Priority Data

Apr. 7, 1989 [DE] Fed. Rep. of Germany ....... 3911303

[51] Int. Cl.⁵ .............................................. A61C 17/32
[52] U.S. Cl. ............................................ 15/22.1; 15/23; 81/467; 192/56 R; 403/351
[58] Field of Search .................... 15/22.1, 22.2, 22.4, 15/23, 24, 28, 29, 97.1; 192/56 R; 74/412 TA; 81/46.7, 473, 474, 476; 464/35; 403/351

[56] References Cited

U.S. PATENT DOCUMENTS

| | | |
|---|---|---|
| 2,805,529 | 9/1957 | Mathes ............................... 15/23 |
| 2,881,602 | 4/1959 | Baker et al. ........................ 464/35 |
| 3,145,404 | 8/1964 | Fiedler ................................ 15/23 |
| 3,278,963 | 10/1966 | Bond ................................. 15/22.1 |
| 3,574,878 | 4/1971 | Shames et al. ..................... 464/35 |
| 4,420,851 | 12/1983 | Wiener .............................. 15/22.1 |
| 4,610,340 | 9/1986 | Helmes et al. ..................... 464/35 |
| 4,698,869 | 10/1987 | Mierau et al. .................... 15/22.1 |

FOREIGN PATENT DOCUMENTS

| | | |
|---|---|---|
| 0173150 | 8/1985 | European Pat. Off. . |
| 3117160 | 11/1982 | Fed. Rep. of Germany . |
| 3342374 | 4/1984 | Fed. Rep. of Germany . |
| 3301865 | 7/1984 | Fed. Rep. of Germany ......... 15/23 |
| 1166284 | 11/1958 | France ................................ 464/35 |
| 443755 | 1/1949 | Italy ................................... 15/23 |
| 0609238 | 2/1979 | Switzerland ...................... 15/22.1 |
| 0431875 | 7/1935 | United Kingdom ................ 464/35 |

Primary Examiner—Edward L. Roberts
Attorney, Agent, or Firm—Fish & Richardson

[57] ABSTRACT

The invention is directed to a toothbrush having a brush head 26 moved by an electromotive drive 12. It is suggested to arrange a mechanical torque limiting device 15 including a cam follower 13, 14 which is acted upon by a spring 16, 17 between a drive shaft of the electromotive drive 12 and the brush head 26. The user of the toothbrush and the electric motor 12 of the toothbrush are thereby protected against damage resulting from an improper manipulation of the toothbrush.

20 Claims, 3 Drawing Sheets

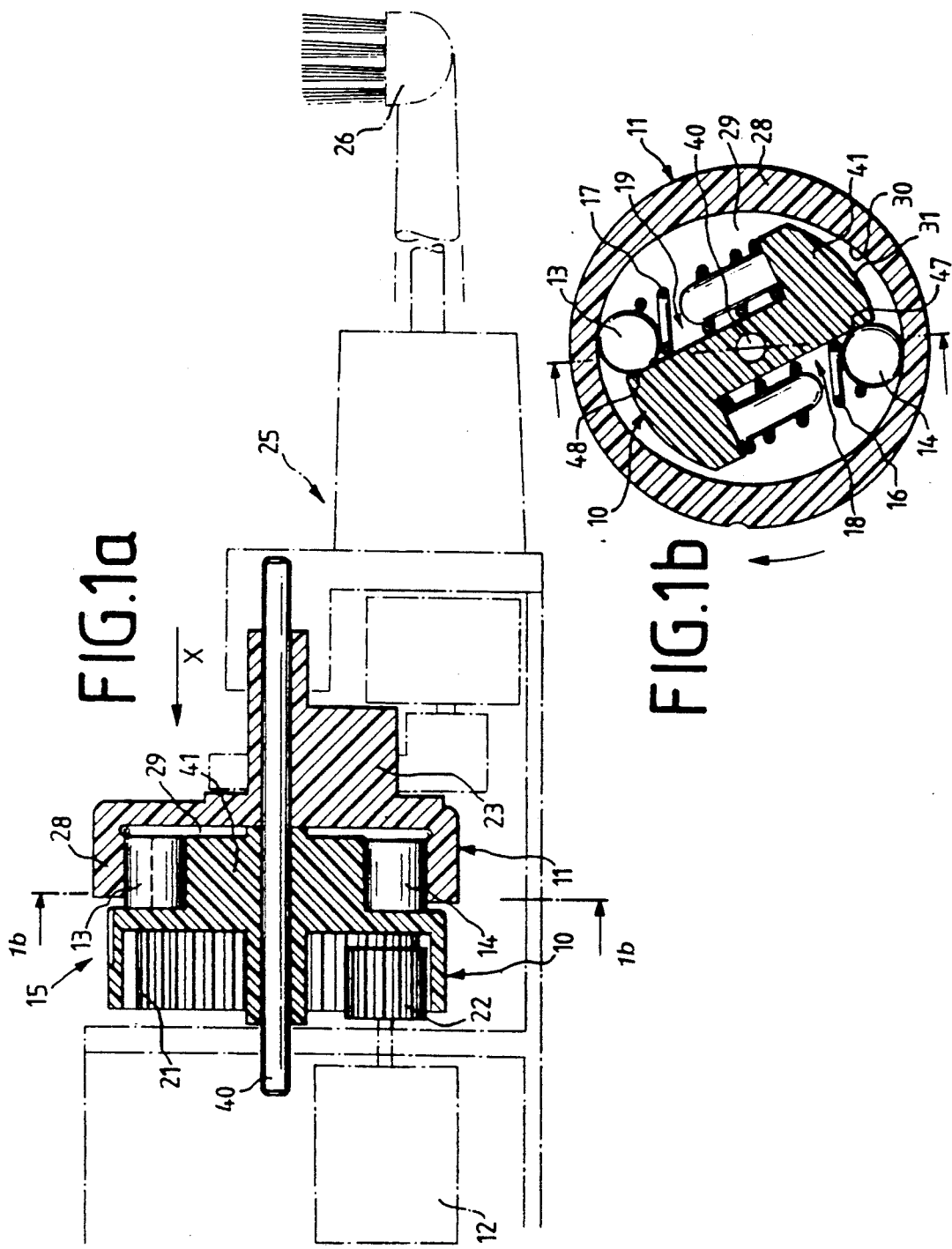

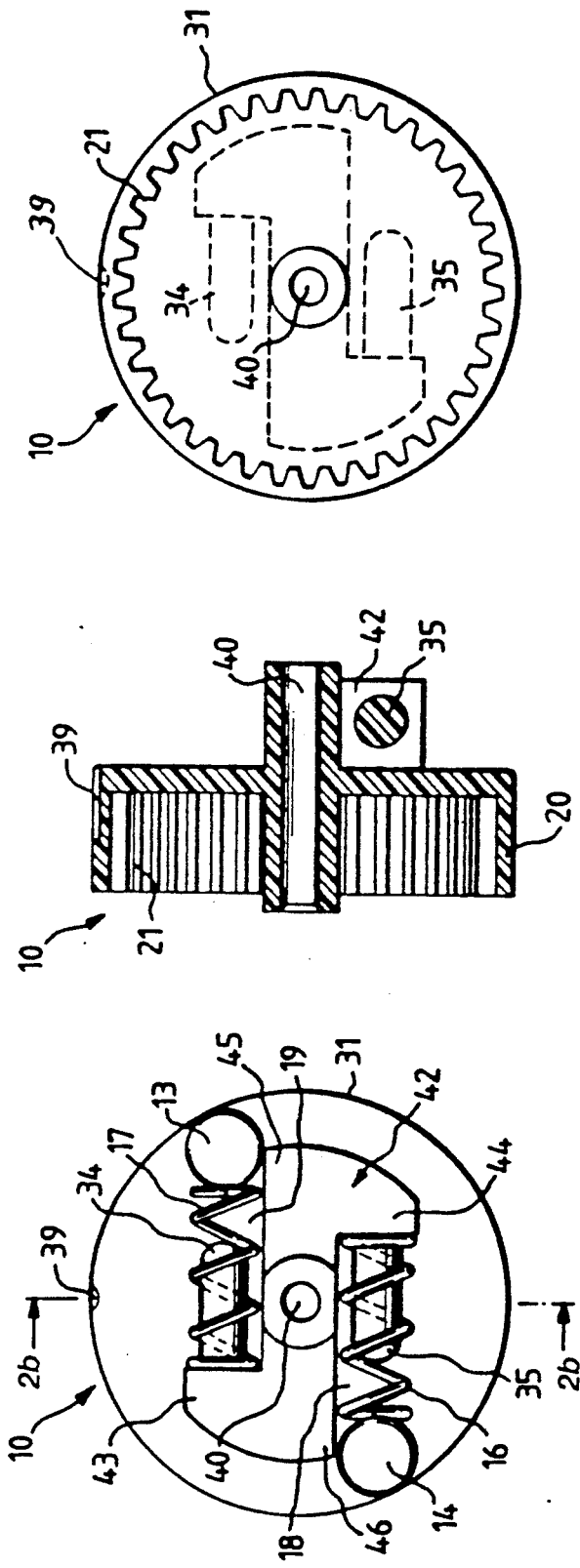

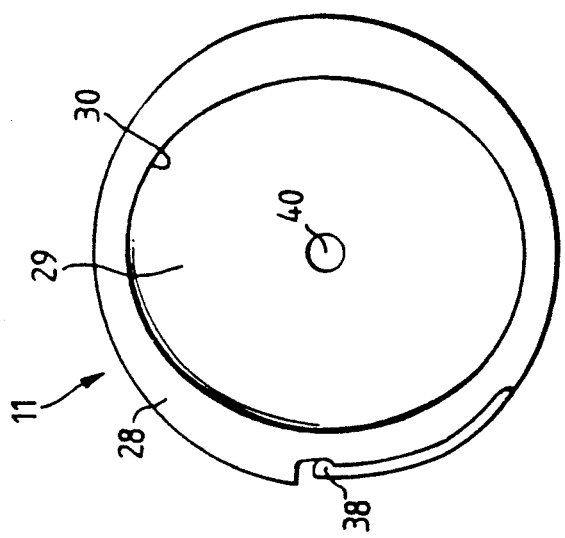
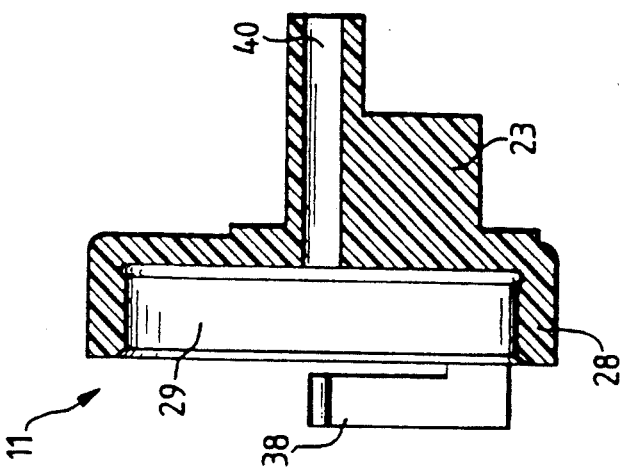
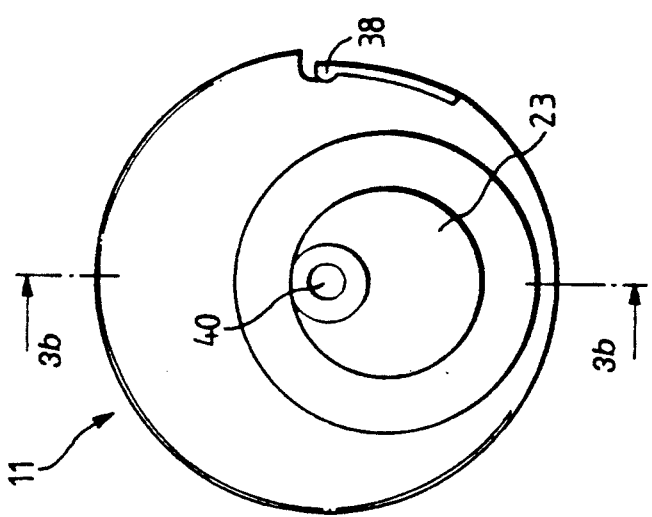

TOOTHBRUSH WITH A BRUSH HEAD MOVED BY AN ELECTROMOTIVE DRIVE MEANS

This invention relates to a toothbrush of the type referred to in the preamble of the main claim. A toothbrush of this type is already known from a plurality of printed publications including, for example, EP-A2 0 173 150. Although, overall, these toothbrushes are well-proven and also established in practice, their handling is still capable of further improvement. One problem exists in protecting the user against the consequences of an improper handling of the toothbrush. Improper handling of the toothbrush is frequently involved if the user, in an attempt to accomplish an intensive cleaning effect, presses the toothbrush with too much pressure against the teeth and also the gums. Such manipulation may result in damage to the gums and may have other consequences adversely affecting the user.

To solve this problem, suggestions have already been made as represented, for example, in DE-C2 31 17 160. In the toothbrush of this specification, the contact pressure is sensed either by means of a pressure-responsive movement of the oscillating drive within the housing or by means of the amount of bending of the handle or the current consumption of the motor, and a visual indication is provided when the sensed value exceeds or drops below the optimum contact pressure. However, such solutions necessitate a high complexity of sensors and electrical means and, as it appears, have so far been unable to establish themselves in practice. In addition, the user may ignore the visual indication and continue improper manipulation of the toothbrush.

Moreover, these solutions fail to provide an indication of how the electric motor of the toothbrush is protected against overload. In view of the requirements for small dimensions and low weight of the toothbrush, the drive motors are correspondingly dimensioned, operating normally in the upper range of their capacity. Improper manipulation of the toothbrush caused, for example, by the application of an excessive contact pressure, may overload the motor and eventually cause a failure of the motor.

It is an object of the present invention to improve upon a toothbrush identified in the preamble in such a manner as to safeguard both the user and at the same time the toothbrush against the consequences of an improper manipulation of the toothbrush.

This object is accomplished by a toothbrush which incorporates the arrangement of a mechanical torque limiting device including a cam follower which is acted upon by a spring means between a drive shaft of the electric motor and the brush head that ensures that the mechanical torque limiting device takes effect in the event of the brush head exerting an excessive contact pressure on the teeth to be cleaned, the transmission of power between the electric motor and the brush head being thus interrupted. In the presence of an overload condition, the brush head remains motionless, while the electric motor rotates freely under a tolerable load which is adjustable by the mechanical torque limiting device. For one thing, the stoppage of brush head movement in case of overload prevents damage to the user's teeth and gums. At the same time, the user receives a clear signal to reduce the contact pressure. For another thing, the motor is protected against overload in that the transmission of power to the brush head is interrupted. Moreover, the use of any additional electrical means is avoided which is advantageous particularly under the prevailing operating conditions—humidity and contamination.

An application of force substantially radial to a pivot of the torque limiting device advantageously diminishes an axial load on the pivot bearings and reduces friction losses.

Because the torque limiting device includes a first and a second coupling half, with the first coupling half having associated to it at least one cam follower which is urged against an annular wall of a cup-shaped recess of the second coupling half, a low overall height of the torque limiting device is ensured in addition to a low amount of wear resulting from the omission of latching recesses. Configuring the annular wall in the form of an elliptical inner periphery permits a precision adjustment of the maximum torque of the torque limiting device to be transmitted by means of the degree of eccentricity of the ellipse, in combination with the selected spring constant of the spring means acting upon the cam follower. Advantageously, the first coupling half includes a substantially circular periphery, and the center axis of the at least one cam follower and the associated spring means is disposed on a chord which does not intersect the pivot. As a result, the force produced by the spring means and acting upon the cam follower acts also in a tangential direction, rather than exclusively in a radial direction. For one thing, the tangential force component acts as a restoring force to adjust the energetically most favorable position of the first coupling half relative to the second coupling half, thus re-establishing the frictional engagement relationship between the two coupling halves in a rapid and defined manner after the actual contact pressure is reduced to permissible values. For another thing, a wedging or clamping effect of the cam follower between an abutment surface of the first coupling half and the annular wall of the second coupling half is accomplished, provided that the center axis of the cam follower and the associated spring means is inclined at an appropriate angle to the annular wall. This clamping effect increases the efficiency of the torque limiting device in an advantageous manner. The arrangement of two cam followers on the first coupling half in a rotational symmetry of 180° reduces the load on the pivot bearings and consequently wear. Moreover, configuring the cam follower as a cylindrical roll contributes to reducing wear, because the cam follower uses its entire axial length to rest against or roll off relative to the annular wall of the cup-shaped recess of the second coupling half. By arranging for the spring means, which is configured as a cylindrical compression spring, to be held by a mandrel-type projection, mounting of the torque limiting device is facilitated essentially, while at the same time a defined location of the spring means in the torque limiting device following assembly is ensured. Providing one of the coupling halves with a ratchet-type projection which cooperates with a groove-shaped recess on the other coupling half to produce a noise when the torque limiting device takes effect has the advantageous effect that operation of the torque limiting device is accompanied by an audible signal. This signals to the user to ease the contact pressure and thus reduce the torque to be delivered by the toothbrush, provided the user has not done so already because the brush head has stopped moving. Further advantages of the invention will become apparent from the subsequent description of embodiments in conjunction with the accompanying drawings. In the drawings, FIG. 1a is a schematic illustration including a longitudinal section through the pivot of the torque limiting device;

FIG. 1b is a schematic illustration including a cross section of the torque limiting device, taken along the line 16—16 of FIG. 1a;

FIG. 2a is a top plan view of coupling half 10, when viewed in the direction of the arrow x of FIG. 1a;

FIG. 2b is a longitudinal section taken along the line 26—26 of FIG. 2a;

FIG. 2c is a bottom plan view of coupling half 10, when viewed against the direction of arrow x;

FIG. 3a is a top plan view of coupling half 11, when viewed in the direction of the arrow x;

FIG. 3b is a longitudinal section taken along the line 36—36 of FIG. 3a; and

FIG. 3c is a bottom plan view of coupling half 11, when viewed against the direction of arrow x.

Referring now to the drawings, reference numeral 15 designates the torque limiting device which is composed of a first coupling half 10 and a second coupling half 11. Both coupling halves 10, 11 rotate about a common pivot 40. The first coupling half 10 has at the driving end an annular wall 20 with an internal toothing 21 which meshes with a gear 22 of an electromotive drive means 12. On the side remote from the annular wall 20, the first coupling half 10 includes a cylindrical pin 41 in which two chambers 18, 19 are embedded. The center axes of the chambers 18, 19 are congruent with chords of the cylindrical pin 41 which do not intersect the pivot 40. The chambers 18, 19 serve to receive spring means 16, 17 which is the embodiment shown are configured as cylindrical compression springs acting substantially in a direction radial to the pivot 40. The spring means 16, 17 act upon cam followers 13, 14, the spring force causing the followers to be urged against the inner surface of an annular wall 28 of the second coupling half 11. The cam followers may be configured as balls or, preferably, as cylindrical rolls or cylindrical rollers. The annular wall 28 forms the side wall of a cup-shaped recess 29 in the area of the second coupling half 11 close to the first coupling half 10. The inner periphery 30 of the cup-shaped recess 29 is preferably configured as an ellipse, whereas the outer periphery 31 of the pin 41 is of circular shape. On the side of the second coupling half 11 remote from the cup-shaped recess 29, a driven eccentric 23 is provided which cooperates with a gear train 25 not specified in more detail in a manner not shown in the Figure. At the driven end, the gear train 25 causes movement of a brush head 26. For purposes of the invention, it is irrelevant which movements the brush head 26 executes in detail, it may be a rotary, oscillating, elliptical or lifting movement, or a combination of any such movements. The essential point is that a mechanical torque limiting device 15 with a cam follower 13, 14 acted upon by a spring means 16, 17 is arranged between the electromotive drive means 12 and the brush head 26. The operation of the torque limiting device 15 described is as follows:

In the event of the load placed on the brush head 26 being zero or low, the torque to be transmitted by the torque limiting device 15 is low; The first coupling half 10 and the second coupling half 11 will then assume such a relative position that the cam followers 13, 14 come to lie approximately on the large semiaxis of the elliptical inner periphery 30. Because the force of the spring means 16, 17 bearing on the cam followers 13, 14 also experiences a force component acting tangentially to the pivot 40, which force component is due to the not exclusively, but only substantially, radial arrangement of the chambers 18, 19, a continuously acting restoring force is ensured in any position of the first coupling half 10 relative to the second coupling half 11. This restoring force causes the two coupling halves to assume at all times the energetically most favorable relative position. Owing to the non-radial arrangement of the chambers, an additional wedging or clamping effect of the cam follower 13, 14 is obtained between a respective side wall area 48, 47 of the chambers and the inner surface of the annular wall 28, provided that rotation of the torque limiting device 15 occurs in clockwise direction as shown in FIG. 1b. As a result, the torque limiting device takes effect also in the event of the inner periphery 30 of the annular wall 28 being circular.

An increase in the torque to be delivered by the toothbrush by increasing, for example, the contact pressure of the brush head 26 against the teeth to be cleaned results in a turning motion of the first coupling half 10 relative to the second coupling half 11 in the direction of the small semiaxis of the elliptical inner periphery 30 and in a compression of the spring means 16, 17 configured as cylindrical compression springs. If the required torque exceeds an adjustable maximum value because, for example, the contact pressure of the brush head 26 against the teeth to be cleaned is too high, this causes a turning motion of the cam followers 13, 14 of the first coupling half 10 beyond the small semiaxis of the elliptical inner periphery 30, thus resulting in a rotation of the first coupling half 10 relative to the second coupling half 11 which remains motionless. Movement of the brush head 26 will then be stopped. If the required torque is reduced again because, for example, the user becomes aware of an improper manipulation of the toothbrush since the brush head 26 has stopped moving, the second coupling half 11 is again caused to rotate, causing also the brush head 26 to perform the desired cleaning movements.

In FIGS. 2 and 3, the first coupling half 10 and the second coupling half 11 of FIG. 1 are shown in detail, like parts being assigned like reference numerals. Unlike FIG. 1, the first coupling half 10 includes, in lieu of the cylindrical pin 41, an elevation 42 in double-L shape with mandrel-type projections 34, 35 formed integral with its short legs 43, 44. These projections 34, 35 serve the function of supporting the spring means 16, 17 which are configured as cylindrical compression springs of which only one spring means 17 is shown for clarity of illustration. The cam followers 13, 14 which are preferably configured as cylindrical rolls are acted upon by the spring means 16, 17 and bear against the end portions 45, 46 of the long legs of the elevation 42. Provided on the outer wall of the first coupling half 10 is a groove-shaped recess 39 which cooperates with a ratchet-type projection 38 on the second coupling half 11. In the event of the torque limiting device 15 interrupting the transmission of power, the first coupling half 10 will rotate relative to the second coupling half 11 which is at rest. On each rotation, the ratchet-type projection 38 will engage the groove 39, producing a rattling noise which is additional to the standstill condition of the brush head 26 and signals equally that an improper handling of the toothbrush is involved.

By introducing the torque limiting device 15 between a drive shaft of the electromotive drive means 12 and the brush head 26, not only the drive means 12 is protected from overload but also the user of the toothbrush is safeguarded against the consequences of improper manipulation, including in particular an excessive contact pressure of the brush head 26 against the teeth to be cleaned.

I claim:

1. A toothbrush comprising
electromotive drive structure,
brush head structure,
drive structure between said electromotive drive structure and said brush head structure for coupling said electromotive drive structure to said brush head structure in driving relation, said drive structure including mechanical torque limiting structure that comprises a first coupling half with annular inner peripheral wall surface structure of elliptical configuration, and
a second coupling half cooperating with said first coupling half and including cam follower structure, and spring structure for biasing said cam follower structure against said annular inner peripheral wall surface structure of said first coupling half for limiting transmission of torque by said drive structure to said brush head structure.

2. The toothbrush as claimed in claim 1 wherein said drive structure is rotatable about a drive axis, and said spring structure urges said cam follower in a direction substantially radial to said drive axis.

3. The toothbrush as claimed in claim 2 wherein said annular wall structure forms the side wall of a cup-shaped recess of said first coupling half.

4. The toothbrush as claimed in claim 3 wherein said second coupling half includes a substantially circular outer periphery and is mounted for rotation about a coupling axis, and said spring structure urges said cam follower along a chord which does not intersect said coupling axis.

5. The toothbrush as claimed in claim 4 wherein said second coupling half includes two of said cam followers, each with an associated spring structure, that are symmetrically arranged on said second coupling half.

6. The toothbrush as claimed in claim 1 wherein said cam follower is a cylindrical roll.

7. The toothbrush as claimed in claim 1 wherein said spring structure is a cylindrical compression spring and said second coupling half includes a mandrel-type projection on which said compression spring is held.

8. The toothbrush as claimed in claim 1 wherein one of said coupling halves includes a recess and the other coupling half includes a ratchet-type projection which cooperates with said recess to produce audible noise when said torque limiting structure takes effect.

9. A toothbrush comprising
electromotive drive structure,
brush head structure,
drive structure between said electromotive drive structure and said brush head structure and rotatable about a drive axis for coupling said electromotive drive structure to said brush head structure in driving relation, said drive structure including mechanical torque limiting structure that comprises a first coupling half with annular wall surface structure, and
a second coupling half cooperating with said first coupling half and including cam follower structure, and spring structure for biasing said cam follower structure against said annular wall surface structure of said first coupling half for limiting transmission of torque by said drive structure to said brush head structure, said spring structure urging said cam follower structure along a chord in a direction that is substantially radial to and does not intersect said drive axis.

10. The toothbrush as claimed in claim 9 wherein said annular wall surface structure includes an elliptical inner peripheral surface.

11. The toothbrush as claimed in claim 9 wherein said second coupling half includes two of said cam followers, each with an associated spring structure, that are symmetrically arranged on said second coupling half.

12. The toothbrush as claimed in claim 11 wherein said spring structure urges said cam follower in a direction substantially radial to said drive axis.

13. The toothbrush as claimed in claim 12 wherein said spring structure is a cylindrical compression spring and said second coupling half includes a mandrel-type projection on which said compression spring is held.

14. The toothbrush as claimed in claim 13 wherein said cam follower is a cylindrical roll.

15. The toothbrush as claimed in claim 14 wherein one of said coupling halves includes a recess and the other coupling half includes a ratchet-type projection which cooperates with said recess to produce audible noise when said torque limiting structure takes effect.

16. The toothbrush as claimed in claim 13 wherein said annular wall surface structure includes an elliptical inner peripheral surface.

17. A toothbrush comprising
electromotive drive structure,
brush head structure,
drive structure between said electromotive drive structure and said brush head structure for coupling said electromotive drive structure to said brush head structure in driving relation, said drive structure including mechanical torque limiting structure that comprises a first coupling half with annular inner peripheral wall surface structure of elliptical configuration,
a second coupling half cooperating with said first coupling half and including cam follower structure, and spring structure for biasing said cam follower structure against said annular inner peripheral wall surface structure of said first coupling half for limiting transmission of torque by said drive structure to said brush head structure, a groove-shaped recess on one of said coupling halves and a ratchet-type projection on the other of said coupling halves for cooperation with said groove-shaped recess to produce an audible noise when said coupling halves move relative to one another with torque limiting effect.

18. The toothbrush as claimed in claim 17 and further including a resilient arm member on which said ratchet-type projection is mounted.

19. The toothbrush as claimed in claim 17 wherein said second coupling half includes two of said cam followers, each with an associated spring structure, that are symmetrically arranged on said second coupling half, said second coupling half includes a substantially circular outer periphery and is mounted for rotation about a coupling axis, and each said spring structure urges its associated said cam follower along a chord which does not intersect said coupling axis.

20. The toothbrush as claimed in claim 19 wherein said cam follower is a cylindrical roll, said spring structure is a cylindrical compression spring and said second coupling half includes a mandrel-type projection on which said compression spring is held.

* * * * *